United States Patent
van der Weide

(10) Patent No.: US 7,467,015 B2
(45) Date of Patent: Dec. 16, 2008

(54) SEGMENTED CATHETER FOR TISSUE ABLATION

(75) Inventor: Daniel Warren van der Weide, Madison, WI (US)

(73) Assignee: Neuwave Medical, Inc., Madison, WI (US)

( * ) Notice: Subject to any disclaimer, the term of this patent is extended or adjusted under 35 U.S.C. 154(b) by 24 days.

(21) Appl. No.: 11/237,136

(22) Filed: Sep. 28, 2005

(65) Prior Publication Data

US 2006/0189973 A1 Aug. 24, 2006

Related U.S. Application Data

(63) Continuation-in-part of application No. 10/834,802, filed on Apr. 29, 2004, now Pat. No. 7,101,369.

(60) Provisional application No. 60/710,815, filed on Aug. 24, 2005, provisional application No. 60/710,276, filed on Aug. 22, 2005, provisional application No. 60/707,797, filed on Aug. 12, 2005, provisional application No. 60/702,393, filed on Jul. 25, 2005, provisional application No. 60/690,370, filed on Jun. 14, 2005, provisional application No. 60/684,065, filed on May 24, 2005, provisional application No. 60/679,722, filed on May 10, 2005.

(51) Int. Cl.
*A61F 2/00* (2006.01)
*A61N 1/06* (2006.01)

(52) U.S. Cl. ............ 607/101; 607/154; 607/156

(58) Field of Classification Search ............ 607/101, 607/102, 154, 156
See application file for complete search history.

(56) References Cited

U.S. PATENT DOCUMENTS

| | | | |
|---|---|---|---|
| 3,800,552 | A | 4/1974 | Sollami |
| 3,838,242 | A | 9/1974 | Goucher |
| 3,991,770 | A | 11/1976 | LeVeen |
| 4,057,064 | A | 11/1977 | Morrison |
| 4,074,718 | A | 2/1978 | Morrison |
| 4,312,364 | A | 1/1982 | Convert |
| 4,375,220 | A | 3/1983 | Matvias |
| 4,446,874 | A | 5/1984 | Vaguine |
| 4,534,347 | A | 8/1985 | Taylor |
| 4,557,272 | A | 12/1985 | Carr |

(Continued)

FOREIGN PATENT DOCUMENTS

EP 1186274 3/2002

(Continued)

OTHER PUBLICATIONS

International Search Report, PCT/US2006,017981, dated Sep. 7, 2006.

(Continued)

*Primary Examiner*—Michael Peffley
(74) *Attorney, Agent, or Firm*—Casimir Jones S.C.

(57) ABSTRACT

A near-field antenna structure is described that is an effective delivery tool for radiofrequency (RF) and microwave power to achieve coagulative necrosis in metastatic tumors while reducing or eliminating thermal conduction along the structure. This tool is a probe small enough to be used safely virtually anywhere in the neck, chest, abdomen, and pelvis, and be guided by computerized tomography (CT) or ultrasonic imaging.

13 Claims, 3 Drawing Sheets

U.S. PATENT DOCUMENTS

| | | | |
|---|---|---|---|
| 4,589,424 A | 5/1986 | Vaguine | |
| 4,621,642 A | 11/1986 | Chen | |
| 4,627,435 A | 12/1986 | Hoskin | |
| 4,643,186 A | 2/1987 | Rosen | |
| 4,662,383 A | 5/1987 | Sogawa | |
| 4,712,559 A * | 12/1987 | Turner | 607/99 |
| 4,776,086 A | 10/1988 | Kasevich | |
| 4,790,311 A | 12/1988 | Ruiz | |
| 4,901,719 A | 2/1990 | Trenconsky | |
| 5,026,959 A | 6/1991 | Ito | |
| 5,057,104 A | 10/1991 | Chess | |
| 5,057,106 A | 10/1991 | Kasevich | |
| 5,074,861 A | 12/1991 | Schneider | |
| RE33,791 E | 1/1992 | Carr | |
| 5,098,429 A | 3/1992 | Sterzer | |
| 5,129,396 A | 7/1992 | Rosen | |
| 5,167,619 A * | 12/1992 | Wuchinich | 604/22 |
| 5,211,625 A | 5/1993 | Sakurai | |
| 5,248,312 A | 9/1993 | Langberg | |
| 5,275,597 A * | 1/1994 | Higgins et al. | 606/33 |
| 5,277,201 A | 1/1994 | Stern | |
| 5,281,213 A | 1/1994 | Milder | |
| 5,281,217 A | 1/1994 | Edwards | |
| 5,344,418 A | 9/1994 | Ghaffari | |
| 5,344,435 A | 9/1994 | Turner | |
| 5,348,554 A | 9/1994 | Imran | |
| 5,358,515 A | 10/1994 | Hurter | |
| 5,364,392 A | 11/1994 | Warner | |
| 5,366,490 A | 11/1994 | Edwards | |
| 5,369,251 A | 11/1994 | King | |
| 5,405,346 A | 4/1995 | Grundy | |
| 5,431,649 A | 7/1995 | Muller | |
| 5,433,740 A | 7/1995 | Yamaguchi | |
| 5,462,556 A | 10/1995 | Powers | |
| 5,480,417 A * | 1/1996 | Hascoet et al. | 607/101 |
| 5,507,743 A | 4/1996 | Edwards | |
| 5,531,677 A | 7/1996 | Lundquist | |
| 5,575,794 A | 11/1996 | Walus | |
| 5,591,227 A | 1/1997 | Dinh | |
| 5,599,295 A | 2/1997 | Rosen | |
| 5,599,352 A | 2/1997 | Dinh | |
| 5,603,697 A | 2/1997 | Grundy et al. | |
| 5,620,479 A * | 4/1997 | Diederich | 601/3 |
| 5,647,871 A | 7/1997 | Levine | |
| 5,693,082 A | 12/1997 | Warner | |
| 5,716,389 A | 2/1998 | Walinsky | |
| 5,737,384 A | 4/1998 | Fenn | |
| 5,741,249 A | 4/1998 | Moss | |
| 5,755,752 A | 5/1998 | Segal | |
| 5,759,200 A | 6/1998 | Azar | |
| 5,776,129 A | 7/1998 | Mersch | |
| 5,776,176 A | 7/1998 | Rudie | |
| 5,782,827 A | 7/1998 | Gough | |
| 5,788,692 A | 8/1998 | Campbell | |
| 5,800,494 A | 9/1998 | Campbell | |
| 5,810,803 A | 9/1998 | Moss | |
| 5,810,804 A | 9/1998 | Gough | |
| 5,849,029 A | 12/1998 | Eckhouse | |
| 5,957,969 A | 9/1999 | Warner | |
| 5,995,875 A | 11/1999 | Blewett | |
| 6,002,968 A | 12/1999 | Edwards | |
| 6,012,457 A | 1/2000 | Lesh | |
| 6,016,811 A | 1/2000 | Knopp | |
| 6,044,846 A | 4/2000 | Edwards | |
| 6,056,744 A | 5/2000 | Edwards | |
| 6,067,475 A | 5/2000 | Graves | |
| 6,073,052 A | 6/2000 | Zelickson | |
| 6,083,255 A | 7/2000 | Laufer | |
| 6,097,985 A | 8/2000 | Kasevich | |
| 6,104,959 A | 8/2000 | Spertell | |
| 6,106,524 A | 8/2000 | Eggers | |
| 6,188,930 B1 | 2/2001 | Carson | |
| 6,190,382 B1 | 2/2001 | Ormsby | |
| 6,208,903 B1 | 3/2001 | Richards | |
| 6,223,085 B1 | 4/2001 | Dann | |
| 6,245,062 B1 | 6/2001 | Berube | |
| 6,251,128 B1 | 6/2001 | Knopp | |
| 6,254,598 B1 | 7/2001 | Edwards | |
| 6,273,884 B1 | 8/2001 | Altshuler | |
| 6,273,885 B1 | 8/2001 | Koop | |
| 6,277,113 B1 | 8/2001 | Berube | |
| 6,287,302 B1 | 9/2001 | Berube | |
| 6,306,130 B1 | 10/2001 | Anderson | |
| 6,306,132 B1 | 10/2001 | Moorman | |
| 6,312,427 B1 | 11/2001 | Berube | |
| 6,325,796 B1 * | 12/2001 | Berube et al. | 606/33 |
| 6,355,033 B1 | 3/2002 | Moorman | |
| 6,364,876 B1 | 4/2002 | Erb | |
| 6,383,182 B1 | 5/2002 | Berube | |
| 6,398,781 B1 | 6/2002 | Goble | |
| 6,427,089 B1 | 7/2002 | Knowlton | |
| 6,471,696 B1 | 10/2002 | Berube | |
| 6,500,174 B1 | 12/2002 | Maguire | |
| 6,506,189 B1 | 1/2003 | Rittman | |
| 6,514,249 B1 | 2/2003 | Maguire | |
| 6,524,308 B1 * | 2/2003 | Muller et al. | 606/49 |
| 6,527,768 B2 | 3/2003 | Berube | |
| 6,546,077 B2 | 4/2003 | Chornenky | |
| 6,582,426 B2 | 6/2003 | Moorman | |
| 6,585,733 B2 | 7/2003 | Wellman | |
| 6,622,731 B2 | 9/2003 | Daniel | |
| 6,652,520 B2 | 11/2003 | Moorman | |
| 6,663,625 B1 * | 12/2003 | Ormsby et al. | 606/41 |
| 6,740,107 B2 | 5/2004 | Loeb | |
| 6,749,606 B2 | 6/2004 | Keast | |
| 6,752,767 B2 | 6/2004 | Turovskiy | |
| 6,770,070 B1 | 8/2004 | Balbierz | |
| 6,780,178 B2 | 8/2004 | Palanker | |
| 6,802,840 B2 | 10/2004 | Chin | |
| 6,817,999 B2 | 11/2004 | Berube | |
| 6,823,218 B2 | 11/2004 | Berube | |
| 6,847,848 B2 | 1/2005 | Sterzer | |
| 6,866,624 B2 | 3/2005 | Chornenky | |
| 6,866,663 B2 | 3/2005 | Edwards | |
| 6,869,431 B2 | 3/2005 | Maguire | |
| 6,878,147 B2 | 4/2005 | Prakash | |
| 6,893,436 B2 | 5/2005 | Woodard | |
| 6,918,905 B2 | 7/2005 | Neuberger | |
| 6,957,108 B2 | 10/2005 | Turner | |
| 6,962,586 B2 | 11/2005 | Berube | |
| 6,972,016 B2 | 12/2005 | Hill | |
| 6,976,986 B2 | 12/2005 | Berube | |
| 6,673,068 B1 | 1/2006 | Berube | |
| 7,033,352 B1 | 4/2006 | Gauthier | |
| 7,101,369 B2 | 9/2006 | van der Weide | |
| 7,147,632 B2 | 12/2006 | Prakash | |
| 7,153,298 B1 | 12/2006 | Cohen | |
| 7,160,289 B2 | 1/2007 | Cohen | |
| 7,160,292 B2 | 1/2007 | Moorman | |
| 7,184,824 B2 | 2/2007 | Hashimshony | |
| 7,197,363 B2 | 3/2007 | Prakash | |
| 7,311,703 B2 | 12/2007 | Turovskiy | |
| 7,318,824 B2 | 1/2008 | Prakash | |
| 7,331,960 B2 | 2/2008 | Schaer | |
| 7,381,208 B2 | 6/2008 | van der Walt | |
| 2002/0022836 A1 * | 2/2002 | Goble et al. | 606/34 |
| 2002/0173780 A1 | 11/2002 | Altshuler | |
| 2003/0088242 A1 * | 5/2003 | Prakash et al. | 606/33 |
| 2005/0011885 A1 | 1/2005 | Seghatol | |
| 2005/0075629 A1 | 4/2005 | Chapelon | |
| 2005/0107870 A1 | 5/2005 | Wang | |
| 2005/0149010 A1 | 7/2005 | Turovskiy | |

| | | | |
|---|---|---|---|
| 2005/0165389 A1 | 7/2005 | Swain | |

WO 2004/112628 12/2004

FOREIGN PATENT DOCUMENTS

| EP | 1395190 | 3/2004 |
|---|---|---|
| EP | 1450710 | 9/2004 |
| EP | 1499251 | 1/2005 |
| EP | 1542607 | 6/2005 |
| WO | 03/039385 | 5/2003 |
| WO | 03/088806 | 10/2003 |
| WO | 03/088858 | 10/2003 |
| WO | 2004/004586 | 1/2004 |
| WO | 2004/033039 | 4/2004 |

OTHER PUBLICATIONS

International Search Report, PCT/US2006/033341, dated Aug. 17, 2007.

International Search Report, PCT/US06/032811, dated Jan. 25, 2007.

International Search Report, PCT/US06/031644, dated Aug. 17, 2007.

International Search Report, PCT/US2006/028821, dated Mar. 21, 2007.

International Search Report, PCT/US2005/014534, dated Nov. 29, 2005.

* cited by examiner

SEGMENTED CATHETER FOR TISSUE ABLATION

CLAIM OF PRIORITY

This application is a Continuation-In-Part of U.S. Non-Provisional Patent Application entitled "Triaxial Antenna for Microwave Tissue Ablation" filed Apr. 29, 2004 and assigned U.S. application Ser. No. 10/834,802, now U.S. Pat. No. 7,101,369, the entire disclosure of which is hereby herein incorporated by reference.

This application further claims priority to U.S. Provisional Patent Applications entitled "Segmented Catheter for Tissue Ablation" filed May 10, 2005 and assigned U.S. application Ser. No. 60/679,722; "Microwave Surgical Device" filed May 24, 2005 and assigned U.S. application Ser. No. 60/684,065; "Microwave Tissue Resection Tool" filed Jun. 14, 2005 and assigned U.S. application Ser. No. 60/690,370; "Cannula Cooling and Positioning Device" filed Jul. 25, 2005 and assigned U.S. application Ser. No. 60/702,393; "Intralumenal Microwave Device" filed Aug. 12, 2005 and assigned U.S. application Ser. No. 60/707,797; "Air-Core Microwave Ablation Antennas" filed Aug. 22, 2005 and assigned U.S. application Ser. No. 60/710,276; and "Microwave Device for Vascular Ablation" filed Aug. 24, 2005 and assigned U.S. application Ser. No. 60/710,815; the entire disclosures of each and all of these applications are hereby herein incorporated by reference.

CROSS-REFERENCE TO RELATED APPLICATIONS

This application is related to co-pending U.S. Non-Provisional Patent Application entitled "Triaxial Antenna for Microwave Tissue Ablation" filed Apr. 29, 2004 and assigned U.S. application Ser. No. 10/834,802; and to U.S. Provisional Patent Applications entitled "Segmented Catheter for Tissue Ablation" filed May 10, 2005 and assigned U.S. application Ser. No. 60/679,722; "Microwave Surgical Device" filed May 24, 2005 and assigned U.S. application Ser. No. 60/684,065; "Microwave Tissue Resection Tool" filed Jun. 24, 2005 and assigned U.S. application Ser. No. 60/690,370; "Cannula Cooling and Positioning Device" filed Jul. 25, 2005 and assigned U.S. application Ser. No. 60/702,393; "Intralumenal Microwave Device" filed Aug. 12, 2005 and assigned U.S. application Ser. No. 60/707,797; "Air-Core Microwave Ablation Antennas" filed Aug. 22, 2005 and assigned U.S. application Ser. No. 60/710,276; and "Microwave Device for Vascular Ablation" filed Aug. 24, 2005 and assigned U.S. application Ser. No. 60/710,815; the entire disclosures of each and all of these applications are hereby herein incorporated by reference.

FIELD OF INVENTION

The present disclosure relates to medical instruments for ablating tissue.

BACKGROUND

Radiofrequency (RF) ablation is now being used for minimally invasive focal destruction of malignant tumors. Microwave ablation has many advantages over RF ablation, but has not been extensively applied clinically due to the large probe size (14 gauge) and relatively small zone of necrosis (1.6 cm in diameter) [Seki T, Wakabayashi M, Nakagawa T, et al. Ultrasonically guided percutaneous microwave coagulation therapy for small hepatocellular carcinoma. Cancer 1994;74: 817-825] that is created by the only commercial device (Microtaze, Nippon Shoji, Osaka, Japan. 2.450 MHz, 1.6 mm diameter probe, 70 W for 60 seconds). The large probe size would not be compatible with percutaneous use in the chest, and would only be used with caution in the abdomen.

The basis of this invention is the resonant monopole antenna resulting from exposing a length of the center conductor equal to an electrical length equal to $(2n-1)\lambda/4$, where $n=1,2 \ldots 10$, and is typically $n=1$. In this case, the electric field peaks at the end of the exposed center conductor, and is ideally at a minimum where the outer conductor terminates (FIG. 1).

The volumetric shape of the electric field lines will roughly define the zone of necrosis when a resonant coaxial probe is used as an ablation tool. More precisely, the cross product of electric and magnetic field lines determines the power available to deposit into the tissue surrounding the probe tip.

As an example, given the high dielectric constant of liver tissue ($\epsilon_r=43.03$), the quarter-wave length of the center conductor protrusion for resonance at 2.45 GHz would be 4.66 mm, severely limiting the zone of necrosis. A three-quarter wave long protrusion (approximately 14 mm in physical length), which can be extended by multiple half-wavelengths is preferable.

The protrusion of the outer conductor of a coaxial line is also set to $(2n-1)\lambda/4$, where $n=1,2\ldots$, and is not necessarily the same amount as the inner conductor (FIG. 2). This enforces the zero-electric field boundary condition on the coaxial outer conductor, which becomes the "middle conductor."

SUMMARY

A near-field antenna structure is described that is an effective delivery tool for radiofrequency (RF) and microwave power to achieve coagulative necrosis in metastatic tumors while reducing or eliminating thermal conduction along the structure. This tool is a probe small enough to be used safely virtually anywhere in the neck, chest, abdomen, and pelvis, and be guided by computerized tomography (CT) or ultrasonic imaging.

This structure is resonant at a frequency of interest (a drive frequency), typically one falling in the Industrial, Scientific, and Medical (ISM) band, covering approximately 800 MHz to 6 GHz, where efficient sources of ablative power (e.g. >5 watts output) are available. The antenna structure is comprised of one or more resonant sections of coaxial, triaxial or multi-axial transmission line, forming a multi-section filter that passes the drive frequency with essentially no loss, but is incapable of efficiently conducting power at other frequencies. At the distal end, the interior conductor(s) extend from the more exterior conductors in a telescoping fashion at lengths that are resonant at the drive frequency when the catheter is inserted into the tissue to be ablated.

A particular object of the present invention is to limit the conductive path for heat generated both at the ablation site and along the filter sections so that heat travel from the distal end of the catheter to the proximal end is minimized or eliminated. By segmenting the catheter into one or more divisions, each division itself being a resonant length, electric-field coupling between adjacent segments can be preserved while interrupting the path for thermal conduction. The segmented catheter is reinforced with non-conducting materials in the gaps between segments, as well as (optionally) with a stiff inner conductor wire, thus preserving mechanical stability needed for insertion.

The preferred embodiment is a resonant coaxial, triaxial or multiaxial structure whose resonant lengths are set 2.45 GHz in the tissue of interest; the catheter can be readily impedance-matched to the tissue by adjusting the length of its coaxial center conductor with respect to its shield, which itself can fit inside one or more introducer needles of total diameter less than 12 gauge. Impedance matching to tissue is done iteratively, using a RF or microwave network analyzer to achieve a low power reflection coefficient. Because its microwave reflection coefficient is low (typically −40 dB or better), the catheter can deliver ~100 W of power to the tissue with minimal heating of the catheter shaft, creating focal zones of coagulative necrosis >3 cm in diameter in fresh bovine liver. To achieve high power economically, we can use a magnetron power supply, with a waveguide-to-coaxial transition and a dual-directional coupler to measure incident and reflected power during the experiment.

To achieve larger zones of necrosis, multiple triaxial probes can be deployed using either a switch or power splitter to distribute the RF or microwave power.

Numerous other advantages and features of the disclosure will become readily apparent from the following detailed description, from the claims and from the accompanying drawings in which like numerals are employed to designate like parts throughout the same.

BRIEF DESCRIPTION OF THE DRAWINGS

A fuller understanding of the foregoing may be had by reference to the accompanying drawings wherein.

DESCRIPTION OF DISCLOSED EMBODIMENT

Figure 1:
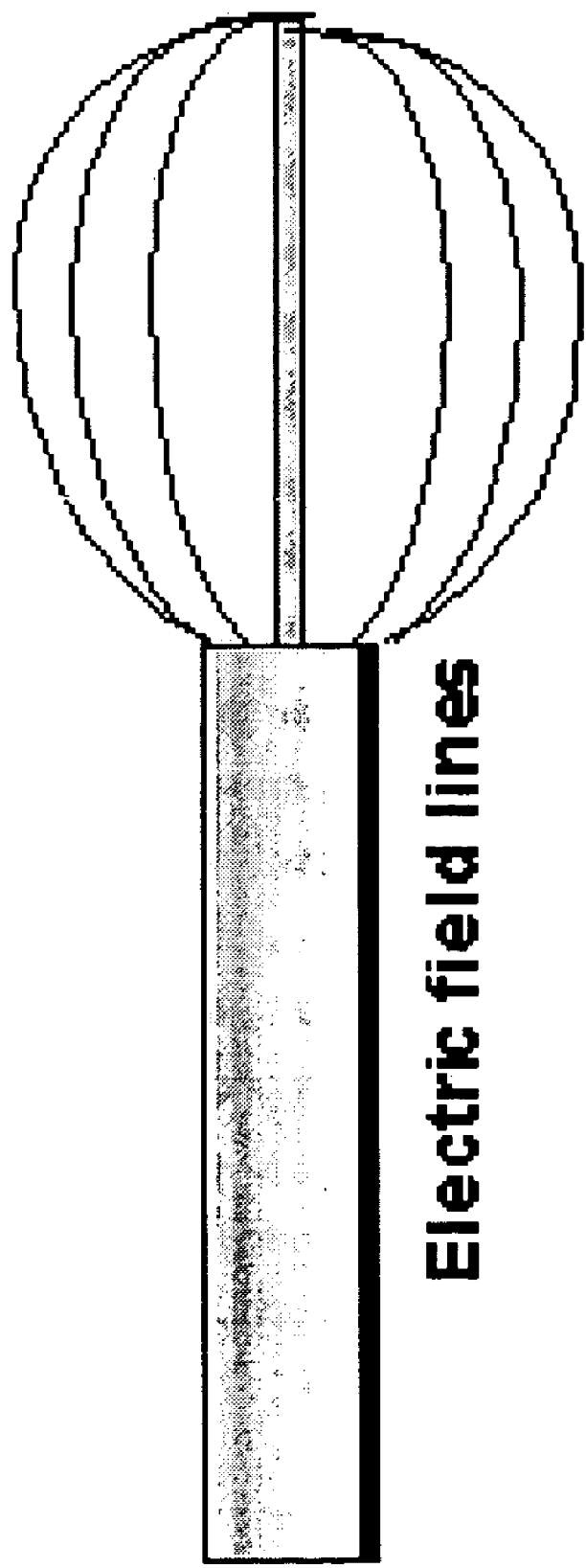
FIG. 1 is diagram of a quarter-wave resonant coaxial probe and associated electric field lines.

While the invention is susceptible of embodiment in many different forms, there is shown in the drawings and will be described herein in detail one or more embodiments of the present disclosure. It should be understood, however, that the present disclosure is to be considered an exemplification of the principles of the invention, and the embodiment(s) illustrated is/are not intended to limit the spirit and scope of the invention and/or the claims herein.

Segmented Resonant Catheter

Figure 3:
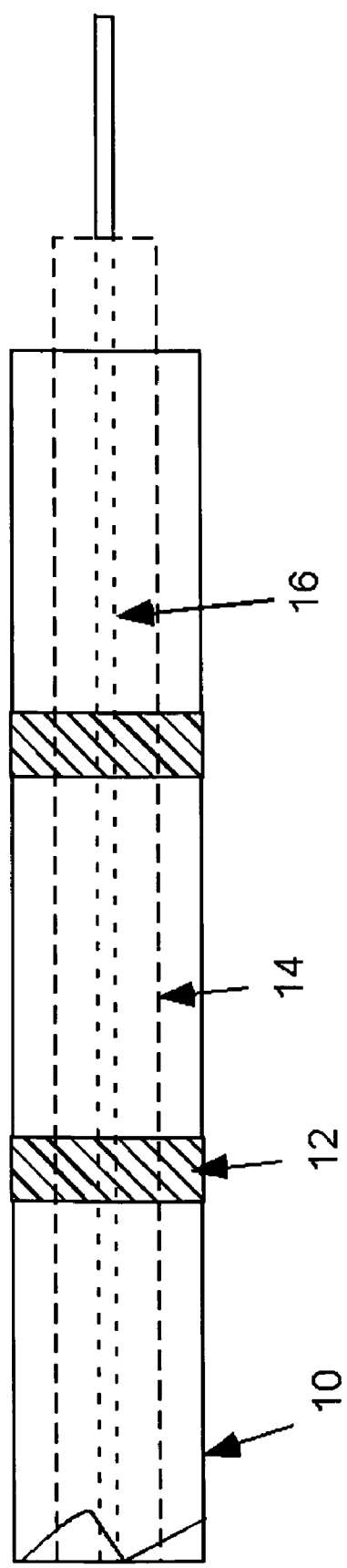
FIG. 3 is a diagram of a segmented resonant catheter of the preferred embodiment of the present invention.

According to FIG. 3, the segmented resonant catheter consists of an outer sheath (10) and subsequent inner conductors (14) and (16), with a triaxial design as the preferred embodiment, though multi-axial designs are also contemplated within the scope of the invention. Conjoining the metallic resonant segments (10) and (14) [and optionally (16)] are dielectric bridges (12) whose thickness and permittivities are set to result in resonance at the drive frequency in the tissue of interest; the drive frequency in the preferred embodiment is 2.45 GHz.

These dielectric bridges (12) are comprised of epoxy, ceramic, Teflon, delrin, or other suitable materials, and with appropriate internal stiffening from dielectric sleeves, can even be air.

Results from Segmented Resonant Catheter

A principal object of the present invention is to reduce thermal conduction along the catheter while preserving or even enhancing the microwave resonance that minimizes reflected microwave power. This is done by separating the outer conductors (and optionally, the center conductor) of the catheter into one or more segments of a resonant length (typically $\lambda/2$), starting from the distal end of the catheter, using a dielectric bridge (resin, ceramic, etc) for mechanical stability.

Additional half-wavelength segments along catheter would further improve thermal isolation.

Testing of a Prototype Small Diameter Triaxial Microwave Catheter

Figure 2:
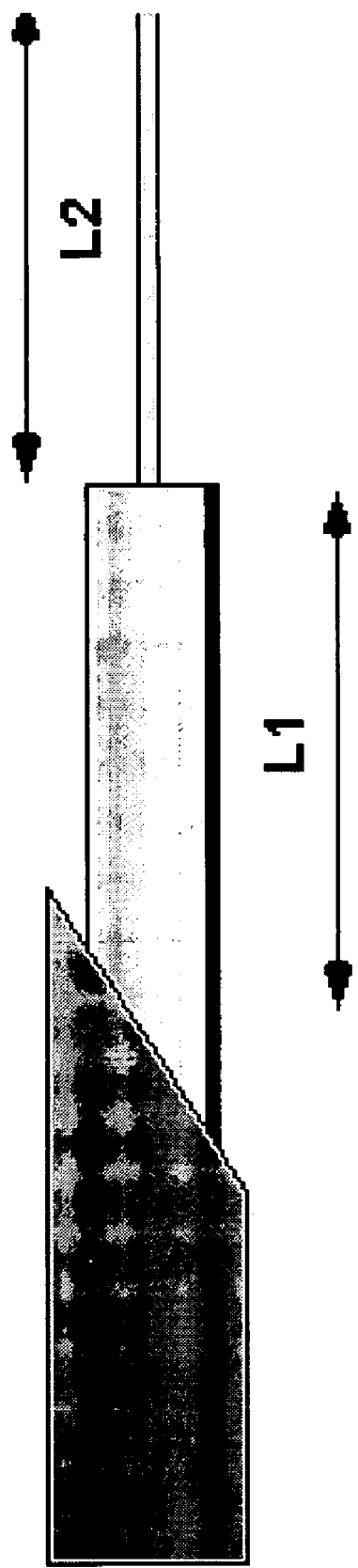
FIG. 2 is a diagram of a triaxial microcatheter arrangement with a needle as the outer conductor. L1 is the average length of the middle conductor protrusion; L2 is the center conductor protrusion.

The applied power ranged from 25 W to 50 W with durations of up to 120 s. Reflected powers were at most −14 dB (i.e. <0.05) of the incident power, and usually −20 dB (0.01 of the incident power). The catheter temperature above the treatment area was only slightly warm to the touch, confirming that almost all the incident power was deposited into the tissue. The reason for this low reflected power is primarily due to careful tuning of the center conductor length (L2 in FIG. 2). This was accomplished by inserting the catheter into liver tissue and measuring the microwave reflection coefficient at 2.45 GHz using a calibrated Hewlett-Packard 8720D vector network analyzer. By trimming length L2 and noting the shift of the fundamental $3\lambda/4$ resonance, small-signal reflected power was <−25 dB. Variation from this value is expected under the large-signal conditions of ablation, as tissue properties change during the procedure.

It is to be understood that the embodiment(s) herein described is/are merely illustrative of the principles of the present invention. Various modifications may be made by those skilled in the art without departing from the spirit or scope of the claims which follow.

What is claimed is:

1. A catheter comprising an outer sheath, wherein said outer sheath comprises a plurality of segments and non-conductive elements, wherein said plurality of segments are successively aligned in a longitudinal manner, wherein each segment is resonant at a drive frequency, wherein each segment has a length of $(2n-1)\lambda/4$ where n is a non-zero positive integer, wherein one of said non-conductive elements is positioned between each of said successively aligned segments, wherein said non-conductive elements permit efficient passage of microwave energy at said drive frequency along said successively aligned segments while inhibiting the passage of power at other frequencies along said successively aligned segments so as to minimize production of thermal energy along said catheter.

2. The catheter of claim 1 having an inner co-axial cable with a center conductor suspended by said non-conductive materials and an air dielectric.

3. The catheter of claim 1 having inner coaxial sections of lengths resonant at a drive frequency.

4. The catheter of claim 1, further comprising a middle conductor and a center conductor; wherein said outer sheath, said middle conductor and said center conductor comprise a triaxial arrangement.

5. The catheter of claim 1, wherein said outer sheath is a needle.

6. The catheter of claim 4, wherein said middle conductor and said center conductor comprise a co-axial cable.

7. The catheter of claim 1, wherein said drive frequency is 2.45 GHz.

8. The catheter of claim 4, wherein said middle conductor extends from said outer sheath by a length.

9. The catheter of claim 8, wherein said length that the middle conductor extends from said outer sheath is $(2n-1)\lambda/4$ where n is a non-zero positive integer.

10. The catheter of claim 8, wherein said center conductor extends from said middle conductor by a length.

11. The catheter of claim 10, wherein said length that said center conductor extends from said middle conductor is $(2n-1)\lambda/4$ where n is a non-zero positive integer.

12. The catheter of claim 11, wherein n equals 2.

13. The catheter of claim 1, wherein said non-conductive elements are configured to reduce heat generated at an ablation site by a distal end of said catheter from traveling to a proximal portion of said catheter.

* * * * *